United States Patent [19]

Loyd et al.

[11] Patent Number: 5,298,406

[45] Date of Patent: Mar. 29, 1994

[54] FORMULATION FOR STABILIZING ENZYMATIC ACTIVITY AND IMMUNOREACTIVITY OF CREATINE KINASE AND CREATINE KINASE ISOENZYMES

[75] Inventors: Joseph E. Loyd, Landenberg, Pa.; Barbara A. Search, Newark, Del.

[73] Assignee: E. I. Du Pont de Nemours and Company, Wilmington, Del.

[21] Appl. No.: 939,861

[22] Filed: Sep. 14, 1992

[51] Int. Cl.[5] .......................... C12Q 1/50; C12N 9/96; C12N 9/12

[52] U.S. Cl. ...................... 435/17; 435/188; 435/194

[58] Field of Search ................... 435/17, 188, 194

[56] References Cited

U.S. PATENT DOCUMENTS

| | | | |
|---|---|---|---|
| 4,276,376 | 6/1981 | Hundt et al. | 435/17 |
| 4,442,212 | 4/1984 | Briggs | 435/188 |
| 4,931,392 | 6/1990 | Rehner et al. | 435/188 |
| 4,994,375 | 2/1991 | Posner et al. | 435/17 |

FOREIGN PATENT DOCUMENTS 9118091 11/1991 World Int. Prop. O.

OTHER PUBLICATIONS

Halliwell, B. et al. "The Antioxidants of Human Extracellular Fluids." Arch. Biochem. Biophys. 280(1) 1-8 (Jul. 1990).

Clin Biochem, vol. 25, pp. 11-13, 1992 Joseph E. Buttery, et al.

*Primary Examiner*—Robert A. Wax
*Assistant Examiner*—Rebecca Prouty

[57] ABSTRACT

A formulation for stabilizing enzymatic activity and immunoreactivity of creatine kinase and creatine kinase isoenzymes comprising animal serum, creatine kinase and/or creatine kinase isoenzymes, an effective amount of a buffer having a pKa in the range of 6.2-7.6 to maintain pH of the formulation at 6.7±0.1, an effective amount of a non-thiol antioxidant to prevent oxidation of creatine kinase or creatine kinase isoenzyme thiol groups, an effective amount of a non-reducing polyol to stabilize immunoreactivity of creatine kinase or creatine kinase isoenzymes, and an effective amount of an antimicrobial to prevent microbial growth is provided.

8 Claims, No Drawings

FORMULATION FOR STABILIZING ENZYMATIC ACTIVITY AND IMMUNOREACTIVITY OF CREATINE KINASE AND CREATINE KINASE ISOENZYMES

TECHNICAL FIELD

This invention relates to a formulation for stabilizing the enzymatic activity and immunoreactivity of creatine kinase and creatine kinase isoenzymes contained in human serum samples and in reconstitutable lyophilized control products used for the determination of creatine kinase or creatine kinase isoenzyme levels in human serum samples.

BACKGROUND ART

The determination of creatine kinase (CK) or CK isoenzyme levels in human serum is important in diagnosing a number of physiological conditions. An increased level of CK can be indicative of myocardial infarction, myocardial ischemia, stenocardia, tachycardia, myocarditis, subarachnoid hemorrage, stroke, brain tumor, meningitis and encephalitis, among other conditions.

Three predominant isoenzymes of CK are recognized; these are dimers consisting of the M and B subunits. The predominant dimer present in the blood, serum or plasma of normal individuals is CK-MM isoenzyme, with variable but usually trace quantities of CK-MB that indicate the normal degradation of skeletal muscle. The CK-BB isoenzyme is not usually present in detectable amounts in serum of normal individuals but is present in significant quantities in brain tissue and smooth muscle tissue.

Elevations of the CK-BB isoenzyme can occur in physiological conditions such as metastatic carcinoma or severe burns. Elevated levels of CK-MB isoenzyme have been used as an indicator of myocardial infarction where possible sources of significant skeletal muscle damage can be eliminated. More particularly, repetitive determinations of CK-MB levels in serum can indicate the time course and severity of infarctions.

More recently, the isoforms of CK isoenzymes have received attention as potential markers for early diagnosis of myocardial infarction. There are three isoforms of CK-MM isoenzyme; CK-MM1, CK-MM2 and CK-MM3; and two isoforms of CK-MB isoenzyme; CK-MB1 and CK-MB2. Shortly after myocardial infarction, the ratio of CK-MM and CK-MB isoforms contained in tissue to that contained in plasma increases. Such increase occurs several hours before either total CK or CK-MB activity exceeds normal reference values.

A number of diagnostic assays have been developed for the determination of the presence or the concentration of CK or CK isoenzymes in human serum. Many such assays are based on measurement of the enzymatic activity of the CK enzyme or isoenzyme. Difficulties in measuring the enzymatic activity of the CK-MB isoenzyme and the need for greater sensitivity have led to the development of immunochemical mass determinations for CK-MB. Such assays are highly dependent on the immunoreactivity of the CK-MB isoenzyme.

It has been observed that CK and CK isoenzymes are highly unstable. CK and CK isoenzymes are sulfhydryl-requiring, that is, they need to maintain their —SH groups in their free, unoxidized form. Atmospheric oxygen causes the oxidation of the —SH groups to the disulfide linkage, thereby diminishing enzyme stability and catalytic activity. Additionally, changes to the CK and CK isoenzyme molecules caused by increased temperatures and the presence of proteases and reducing agents can change the immunoreactivity of the molecules.

Storage stability of patient serum samples containing CK and CK isoenzymes is important, especially when further analysis on a sample is requested retrospectively following an equivocal ECG or when the cause of a raised total CK level is being sought. Such a request may be made the same day or days after the initial ECG or CK assay was performed. Buttery et al. [Clinical Biochemistry, 25: 11-13 (1992)] report that samples stored at $-20°$ C. overnight show, on average, a decrease in CK-MB isoenzyme values of 13.5%. Such a decrease could result in a misdiagnosis. Prolonged storage of samples at room temperature for 4-6 days showed a 50% deterioration of CK-MB when measured electrophoretically and 20% deterioration when measured by an immunochemical mass assay. Therefore, a need exists for a means for stabilizing CK and CK isoenzyme activity in patient serum samples.

CK and CK isoenzyme assay control products containing CK or CK isoenzyme also suffer from instability problems. In order to facilitate storage of such control products, they are typically lyophilized. A useful lyophilized CK or CK isoenzyme control product must have two characteristics which are often very difficult to achieve simultaneously. First, there must be substantially no or only very small temperature of hydration effect and, second, there must only be very slight changes in enzyme activity or immunoreactivity upon standing after reconstitution (rehydration) of the lyophilized control product. The temperature of hydration effect is the phenomenon of variability of recovered enzyme activity and immunoreactivity from a lyophilized control product upon rehydration caused by the differences in the temperature of water used. For practical purposes, for use in diagnostic assays, lyophilized control products must have a small temperature of hydration effect to permit reproducible analytical results.

Thiols, such as N-acetyl cysteine, glutathione and monothioglycerol, have been used as additives to lyophilized CK and CK isoenzyme control products as thiol protectors. (See U.S. Pat. No. 4,442,212, issued Apr. 10, 1984 to Briggs.) While use of such thiols in lyophilized CK and CK isoenzyme control products has been found to control the stability of CK and CK isoenzyme enzymatic activity after reconstitution, use of thiols has little effect on stability of CK and CK isoenzyme immunoreactivity.

U.S. Pat. No. 4,994,375, issued Feb. 19, 1991 to Posner et al., discloses a stable reconstituted human serum-based control for the assay of total lactate dehydrogenase (LDH) and CK and their isoenzymes which is comprised of human serum, LDH and LDH isoenzymes, CK and CK isoenzymes and sodium citrate. The pH of the control product is adjusted to 6.7 before lyophilization. In this control product formulation, there is no means disclosed for maintaining the pH of the control product at 6.7 after rehydration. Variability in pH of the control product after reformulation can lead to inconsistent results. Additionally, there is no suggestion that the disclosed control product formulation would stabilize immunoreactivity of CK or CK isoenzymes.

There is a need for a formulation for stabilizing enzymatic activity and immunoreactivity of CK and CK isoenzymes which can be used to stabilize human serum samples containing CK and CK isoenzymes and as a reconstitutable lyophilized CK and CK isoenzyme control product which exhibits little temperature of hydration effect and which is stable after reconstitution.

DISCLOSURE OF THE INVENTION

The formulation of this invention for stabilizing enzymatic activity and immunoreactivity of creatine kinase or creatine kinase isoenzymes comprising:
(a) animal serum;
(b) creatine kinase and/or creatine kinase isoenzymes;
(c) an effective amount of a buffer having a pKa in the range of 6.2–7.6 to maintain pH of the formulation at 6.7±0.1;
(d) an effective amount of a non-thiol antioxidant to prevent oxidation of creatine kinase or creatine kinase isoenzyme thiol groups;
(e) an effective amount of a non-reducing polyol to stabilize immunoreactivity of creatine kinase or creatine kinase isoenzymes; and
(f) an effective amount of an antimicrobial to prevent microbial growth in the formulation.

The formulation of the instant invention can be used to stabilize enzymatic activity and immunoreactivity of CK and CK isoenzymes in human serum samples and in reconstitutable lyophilized control products for the assay of CK or CK-MB in human serum. When used as a reconstitutable lyophilized control product, the formulation of the instant invention exhibits little temperature of hydration effect providing a control product in which enzymatic activity and immunoreactivity remain constant after reconstitution for at least two weeks at 4° C.

DESCRIPTION OF THE INVENTION

The formulation of the instant invention is useful for stabilizing both the enzymatic activity and immunoreactivity of CK and CK isoenzymes in human serum samples and in reconstituted lyophilized CK and CK isoenzyme control products. The formulation can take the form of an additive to blood collection tubes for the collection of human serum samples to be assayed for the determination of CK and CK isoenzyme levels or the formulation can take the form of a reconstitutable lyophilized control product to be used in an assay for the determination of CK and/or CK isoenzyme levels.

The formulation of the instant invention is serum-based. Where the formulation is used in blood collection tubes to preserve the stability of CK and CK isoenzymes in human serum samples, the serum is that collected as the sample. Where the formulation takes the form of a reconstitutable lyophilized CK and/or CK isoenzyme control product, the serum can be any animal serum. Horse serum is preferred.

When the formulation is used as a control product, it is preferred that the serum have substantially low or no residual CK and CK isoenzyme enzymatic activity or immunoreactivity. Residual enzymatic activity and immunoreactivity can be removed from the serum by heat treatment of the serum. The serum can be heated to any temperature for a length of time which will denature the CK or CK isoenzyme, such as 56° C. for one hour or 60° C. for one minute. Heat treatment of the serum for one minute at 60° C. is preferred.

CK and CK isoenzymes can be found in the human serum samples collected for assaying for CK and CK isoenzymes or, if the formulation is used as a reconstitutable lyophilized control product, CK and CK isoenzymes can be added to the serum base. If the serum base of the formulation is treated to destroy residual CK and CK isoenzyme enzymatic activity and immunoreactivity, the CK and CK isoenzyme should be added to the serum base after such treatment has occurred. The reconstitutable control product can be a control product for the assay of both CK and CK isoenzymes, in which case, both CK and CK isoenzymes would be present in the formulation. Alternatively, the control product can be used for the assay of only CK or a CK isoenzyme, in which case, only CK or the CK isoenzyme would be present in the formulation. CK or CK isoenzyme from any animal muscle or heart tissue, such as cynamolgus monkey, rabbit and human, can be used when the control product is to be used in conjunction with a diagnostic assay which measures the enzymatic activity of the CK enzyme or isoenzyme. When the diagnostic assay is an immunochemical assay, animal CK or CK isoenzyme which cross-reacts with antibody to human CK or CK isoenzyme can be used. Purified human CK or CK isoenzyme is preferred, regardless of the type of diagnostic assay with which the control product is to be used.

One of the key elements of the formulation of the instant invention is that the formulation pH is maintained at 6.7±0.1, even after reconstitution of the lyophilized control product. Maintenance of the formulation pH is achieved by including a buffer having a pKa in the range of 6.2–7.6. Suitable buffers include piperazine-N,N'-bis(2-ethanesulfonic acid) (PIPES), N-2-acetamidoiminodiacetic acid (ADA), 1,3-bis-[tris(hydroxymethyl)methylamino] propane (BIS-TRIS PROPANE), N-2-acetamido-2-aminoethanesulfonic acid (ACES), imidazole, diethylmalonic acid, N-2-hydroxyethylpiperazine-N'-2-ethanesulfonic acid (HEPES), and phosphate. PIPES buffer is preferred. An effective amount of buffer is the concentration of buffer which is needed to maintain pH of the formulation between 6.6 and 6.8. A PIPES buffer concentration of 80–95 mM has been shown to be effective.

As described above, in order to stabilize CK and CK isoenzyme enzymatic activity and immunoreactivity, it is important to prevent oxidation of the CK and CK isoenyzme thiol groups. The formulation of the instant invention does so by containing a non-thiol antioxidant, such as ascorbic acid, butylated hydroxyanisole (BHA) and butylated hydroxytoluene (BHT). Ascorbic acid is preferred. An effective amount of non-thiol antioxidant is the concentration of antioxidant needed to prevent oxidation of the thiol groups. Concentrations of ascorbic acid in the range of 10–100 mM have been shown to be effective, 30 mM being preferred.

Surprisingly, it was found that inclusion of a non-reducing polyol into the formulation conferred greater stability of CK and CK isoenzyme immunoreactivity. Any non-reducing polyol, such as sucrose, glycerol, trehalose and mannitol, can be used in the formulation of the instant invention. Sucrose is preferred. An effective amount of non-reducing polyol is the concentration of polyol which is needed to stabilize the immunoreactivity of CK and CK isoenzyme. A concentration of non-reducing polyol of 1% or greater has been found to be effective.

Microbial growth can produce proteases and other enzymes which can destroy both enzymatic and antigenic activity of CK and CK isoenzymes. Therefore, an antimicrobial is included in the formulation of the instant invention to prevent microbial growth. Any aminoglycoside antimicrobial, such as gentamicin, streptomycin, neomycin and kanamycin, can be used. Gentamicin is preferred. An effective amount of antimicrobial is the concentration of antimicrobial needed to prevent microbial growth. A 0.1% concentration of gentamicin has been found to be effective.

The formulation of the instant invention can be used to stabilize human serum samples collected in blood collection tubes. Buffer, non-thiol antioxidant, non-reducing polyol and antimicrobial can be added in dry form to blood collection tubes for use in collecting the human serum samples containing CK and CK isoenzymes.

Alternatively, the formulation can be used as a reconstitutable lyophilized control product. All of the components, except CK and CK isoenzyme, can be added in any order to the serum base of the formulation. The formulation can then be pH adjusted to 6.7±0.05, sterile filtered and heat treated, if so desired. CK and CK isoenzyme must be added after pH adjustment and heat treatment so as to avoid destruction of CK and CK isoenzyme. The serum-based formulation can then be lyophilized by any standard lyophilization technique. Since the lyophilized control product is stable, it can be reconstituted with water and used in conjunction with, for example, automated clinical analyzers utilized for the measurement of CK and/or CK isoenzymes. Once reconstituted, the formulation of the instant invention has been found to remain stable for at least two weeks when stored at 4° C.

The following examples illustrate the invention.

EXAMPLES

Example I

Preparation of Reconstitutable Lyophilized CK-MB Calibrators

I. Preparation of CK-MB Calibrator Matrix

To 23 liters of horse serum (Pel-freez Biologicals) was added 616.4 gm of 80 mM PIPES 1.5 Na salt (Sigma Corp.), 23 gm of gentamicin sulfate (Sigma Corp.), 230 gm of sucrose (Ulta Pure) and 121.6 gm ascorbic acid (Calbiochem Corp.) with continuous mixing until all additives were completely dissolved in the horse serum. While stirring vigorously, but not so as to cause foaming, the horse serum mixture was adjusted to a pH of 6.7±0.05 at room temperature by slowly adding sodium hydroxide.

After pH adjustment, the horse serum mixture was filtered through a 0.2-micron filter into a heat treatment tank containing a submersible heating coil. The horse serum mixture was heat treated to remove residual CK and CK isoenzyme by heating the mixture to 60° C. for one minute. Horse serum containing the above-identified additives, adjusted to pH 6.7±0.05, filtered and heat treated is CK-MB Calibrator Matrix. The Matrix was covered and stored refrigerated for further use.

II. Preparation of CK-MB Stock Solution

A lyophilized preparation of CK-MB (Lee Scientific) was used as the source of CK isoenzyme. The lyophilized CK-MB preparation was rehydrated with 16 mL of Calibrator Matrix to prepare CK-MB Stock Solution. To three 100 mL volumetric flasks was added 25 μL of Stock Solution and enough Matrix to bring the resulting solution to 100 mL. These solutions were used as samples on the aca ® plus immunoassay system (E. I. du Pont de Nemours and Company) and analyzed for mass CK-MB content using a mass immunochemical assay. Results of this assay showed that the CK-MB Stock Solution had a CK-MB concentration of 383,000 μg/L.

III. Formulation of CK-MB Calibrator Levels 1, 2, Low, Medium, High and 3

Using the CK-MB concentration of CK-MB Stock Solution determined in Section II., above, it was calculated, using a mass balance equation, that 9.9 gm of CK-MB Stock Solution needed to be added to 9070 gm of Matrix to bring the Matrix to a target CK-MB concentration of 420 μg/L. The Matrix was assayed on the aca ® plus immunoassay system to determine CK-MB concentration. The result was lower than the expected 420 μg/L and an additional 2.3 gm of CK-MB Stock Solution was added to the Matrix. This was designated Calibrator Level 3. Calibrator Matrix alone was used as Calibrator Level 1, containing 0 μg/mL CK-MB. Calibrator Levels High (200 μg/mL), Medium (100 μg/mL), Low (50 μg/mL) and 2 (20 μg/mL) were prepared by mixing together 1414 gm Matrix and 1286 gm Level 3, 2057 gm Matrix and 643 gm Level 3, 2379 gm Matrix and 321 gm Level 3 and 6200 gm Matrix with 310 gm Level 3, respectively.

For each level of CK-MB Calibrator, lyophilization vials were filled with 5.39 gm of calibrator and topped with half-inserted slotted stoppers. The vials were lyophilized according to a routine protocol. The vials were frozen to approximately −38° C. When the condenser reached approximately −80° C., the chamber was evacuated to 200 millitorr and the shelf temperature was gradually increased to 30° C. over approximately 45 hours. The chamber was then held at 30° C. and 30 millitorr for ten hours. The lyophilized vials were stoppered under a vacuum of approximately 30 millitorr and cooled to 4° C.

Example II

Stability Testing of Reconstituted CK-MB Calibrators

One vial each of lyophilized CK-MB Calibrator Levels 1, 2, Low, Medium, High and 3, prepared as described in Example I, were reconstituted with 5.0 mL of room temperature water on each of Days 0, 8, 22 and 44. The reconstituted vials prepared on Days 1, 8 and 22 were stored at 4° C. until Day 44. Calibrator reconstituted on Day 44 served as a control as it contained the original amount of CK-MB in each calibrator level. On Day 44, three replicates of each level of reconstituted CK-MB Calibrator from each day of reconstitution were assayed on the aca ® plus immunoassay system to determine the amount of CK-MB in each CK-MB calibrator level using a mass immunochemical CK-MB method of determination. Means of the replicates, standard deviations and percent coefficients of variation were calculated. Using the slope and intercept calculated from a linear least squares correlation for each level, a percent loss per day was calculated. From the percent loss per day was calculated the number of days from reconstitution until a 5% loss of CK-MB would result for each reconstituted calibrator level. Results are depicted in Table 1, below.

TABLE 1

| LEVEL | DAYS FROM RECONSTITUTION OF FIRST SET | MEAN CK-MB (MAU) | S.D. | % C.V. | % LOSS PER DAY | NUMBER OF DAYS FOR 5% LOSS |
|---|---|---|---|---|---|---|
| 1 | 0 | 34.15 | 1.29 | 3.79 | | |
| 1 | 8 | 34.03 | 0.84 | 2.46 | | |
| 1 | 22 | 34.67 | 0.41 | 1.17 | | |
| 1 | 44 | 34.75 | 1.13 | 3.25 | | |
| 2 | 0 | 63.28 | 0.25 | 0.39 | 0.06 | 77 |
| 2 | 8 | 64.02 | 0.93 | 1.45 | | |
| 2 | 22 | 65.07 | 0.96 | 1.47 | | |
| 2 | 44 | 64.18 | 0.10 | 0.16 | | |
| LOW | 0 | 112.07 | 0.70 | 0.63 | 0.15 | 34 |
| LOW | 8 | 110.07 | 2.85 | 2.59 | | |
| LOW | 22 | 115.23 | 4.22 | 3.66 | | |
| LOW | 44 | 116.10 | 3.90 | 3.36 | | |
| MEDIUM | 0 | 192.35 | 4.17 | 2.17 | 0.22 | 23 |
| MEDIUM | 8 | 202.40 | 5.09 | 2.52 | | |
| MEDIUM | 22 | 207.07 | 6.49 | 3.14 | | |
| MEDIUM | 44 | 211.23 | 3.85 | 1.82 | | |
| HIGH | 0 | 388.95 | 9.97 | 2.56 | 0.19 | 26 |
| HIGH | 8 | 396.63 | 1.76 | 0.44 | | |
| HIGH | 22 | 406.80 | 2.26 | 0.56 | | |
| HIGH | 44 | 421.65 | 11.95 | 2.83 | | |
| 3 | 0 | 850.93 | 5.39 | 0.63 | 0.08 | 64 |
| 3 | 8 | 888.40 | 12.30 | 1.38 | | |
| 3 | 22 | 880.65 | 9.69 | 1.10 | | |
| 3 | 44 | 891.55 | 3.18 | 0.36 | | |

Results shown in Table 1, above, indicate that the reconstitutable lyophilized CK-MB Calibrator of the instant invention will not lose more than 5% of the original amount of CK-MB contained in the calibrator for at least 23 days after reconstitution when stored at 4° C.

Example III

Temperature of Hydration Effect

Three vials for each of Levels 2 and 3 of the CK-MB Calibrator of the instant invention, prepared according to Example I, above, were rehydrated with water; one vial for each of water temperatures of 4°, 25° and 37° C. Also rehydrated at 4°, 25° and 37° C. were samples of lyophilized stripped human serum at low and high levels of CK-MB, prepared according to U.S. Pat. No. 4,264,471, issued to Briggs on Apr. 28, 1981, and commercial CK-MB calibrators and controls from the Tandem®-E CKMB II ImmunoEnzMetric Assay (Hybritech, Inc.), the Stratus® CK-MB Fluorometric Enzyme Immunoassay Kit (Baxter Diagnostics, Inc., Dade Division) and Cala. The reconstituted calibrators and controls were assayed in triplicate for the amount of CK-MB contained therein using the aca® plus immunoassay system and a mass immunochemical method of determination. Mean CK-MB values were determined for each sample and the percent change in CK-MB value from that of the 4° C. rehydrated sample was calculated. Results are depicted in Table 2, below.

TABLE 2

| SAMPLE | CK-MB (ng/mL) | | | % LOSS OF CK-MB | |
|---|---|---|---|---|---|
| | 4° C. | 25° C. | 37° C. | 25° C. | 37° C. |
| INVENTION, LEVEL 2 | 15.2 | 14.9 | 13.8 | 2.0 | 9.2 |
| INVENTION, LEVEL 3 | 340.0 | 324.0 | 318.0 | 4.7 | 6.5 |
| STRIPPED HUMAN SERUM, LOW | 14.6 | 10.9 | 8.0 | 25.3 | 45.2 |
| STRIPPED HUMAN SERUM, HIGH | 268.0 | 222.0 | 170.0 | 17.2 | 36.6 |
| TANDEM ®-E CONTROL, LOW | 15.1 | 14.0 | 14.1 | 7.3 | 6.6 |
| TANDEM ®-E CONTROL, HIGH | 56.3 | 52.7 | 50.8 | 6.4 | 9.8 |
| TANDEM ®-E CALIBRATOR, HIGH | 35.7 | 36.3 | 33.3 | −1.7 | 6.7 |
| STRATUS ® CALIBRATOR, MID | 16.9 | 13.4 | 10.4 | 20.7 | 38.5 |
| STRATUS ® CALIBRATOR, HIGH | 37.9 | 30.0 | 21.7 | 20.8 | 42.7 |
| CALA, MID | 25.8 | 25.3 | 25.1 | 1.9 | 2.7 |
| CALA, HIGH | 60.4 | 58.9 | 57.4 | 2.5 | 5.0 |

As can be seen from Table 2, the reconstitutable lyophilized CK-MB control product of the instant invention exhibit little temperature of hydration effect. It is desirable that the temperature of hydration effect be as small as possible Only the Cala controls exhibited lower temperature of hydration effect than did the calibrators of the instant invention. The Tandem ®-E calibrator and controls performed comparably to the instant invention at 37° C., but worse at 25° C. The Stratus ® and stripped human serum calibrators showed significantly greater temperature of hydration effect than did the reconstitutable lyophilized CK-MB control product of the instant invention. The results for stripped serum show the magnitude of temperature of rehydration effect one could expect without the instant invention.

What is claimed is:

1. A formulation for stabilizing enzymatic activity and immunoreactivity of creatine kinase or creatine kinase isoenzymes comprising:
   (a) animal serum;
   (b) creatine kinase and/or creatine kinase isoenzymes;
   (c) an effective amount of a buffer having a pKa in the range of 6.2–7.6 to maintain pH of the formulation at 6.7±0.1;
   (d) an effective amount of ascorbic acid to prevent oxidation of creatine kinase or creatine kinase isoenzyme thiol groups;
   (e) an effective amount of a non-reducing polyol to stabilize immunoreactivity of creatine kinase or creatine kinase isoenzymes wherein the non-reducing polyol is selected from the group consisting of sucrose, glycerol, trehalose, and mannitol; and
   (f) an effective amount of an antimicrobial to prevent microbial growth in the formulation.

2. The formulation of claim 1 wherein the buffer is selected from the group consisting of piperazine-N,N'-bis(2-ethanesulfonic acid), N-2-acetamidoiminodiacetic acid, 1,3-bis[tris(hydroxymethyl)methylamino] propane, N-2-acetamido-2-aminoethanesulfonic acid, imidazole, diethylmalonic acid, N-2-hydroxyethylpiperazine-N'-2-ethanesulfonic acid and phosphate.

3. The formulation of claim 1 wherein the buffer is piperazine-N,N'-bis(2-ethanesulfonic acid), the non-reducing polyol is sucrose and the antimicrobial is gentamicin.

4. A stable water reconstitutable lyophilized control product for the assay of creatine kinase or creatine kinase isoenzymes comprising:

(a) animal serum having low residual levels of creatine kinase or creatine kinase isoenzyme enzymatic activity and immunoreactivity;
(b) creatine kinase and/or creatine kinase isoenzyme;
(c) an effective amount of a buffer having a pKa in the range of 6.2–7.6 to maintain pH of the formulation at 6.7±0.1;
(d) an effective amount of ascorbic acid to prevent oxidation of creatine kinase or creatine kinase isoenzyme thiol groups;
(e) an effective amount of a non-reducing polyol to stabilize immunoreactivity of creatine kinase or creatine kinase isoenzymes; and
(f) an effective amount of an antimicrobial to prevent microbial growth in the formulation.

5. The water reconstitutable lyophilized control product of claim 4 wherein the animal serum is heat-treated horse serum.

6. The water reconstitutable lyophilized control product of claim 5 wherein the buffer is piperazine-N,N'-bis(2-ethanesulfonic acid), the non-reducing polyol is sucrose and the antimicrobial is gentamicin.

7. A blood collection tube additive for stabilizing enzymatic activity and immunoreactivity of creatine kinase or creatine kinase isoenzymes contained in human serum samples comprising:
(a) an effective amount of a buffer having a pKa in the range of 6.2–7.6 to maintain pH of the formulation at 6.7±0.1;
(b) an effective amount of ascorbic acid to prevent oxidation of creatine kinase or creatine kinase isoenzyme thiol groups;
(c) an effective amount of a non-reducing polyol to stabilize immunoreactivity of creatine kinase or creatine kinase isoenzymes; and
(d) an effective amount of an antimicrobial to prevent microbial growth in the formulation.

8. The blood collection tube additive of claim 7 wherein the buffer is piperazine-N,N'-bis(2-ethanesulfonic acid), the non-reducing polyol is sucrose and the antimicrobial is gentamicin.

* * * * *